United States Patent [19]

Herrera et al.

[11] 4,247,286
[45] Jan. 27, 1981

[54] STRESS-RELIEVING HINGE FOR A DENTAL RESTORATION

[76] Inventors: William R. Herrera, 775 Ernest Dr., Santa Paula, Calif. 93060; Alex F. Presley, 177 El Pajaro, Vallecito Mobile Home Estates, Newbury Park, Calif. 91320

[21] Appl. No.: 53,753

[22] Filed: Jul. 2, 1979

[51] Int. Cl.³ ............................................. A61C 13/28
[52] U.S. Cl. .................................................. 433/170
[58] Field of Search ................................ 433/169, 170

[56] References Cited

U.S. PATENT DOCUMENTS

| | | | |
|---|---|---|---|
| 1,433,770 | 10/1922 | Wolfe | 433/190 |
| 1,599,361 | 9/1923 | Henderson | 433/190 |
| 2,611,957 | 9/1952 | Baca et al. | 433/170 |
| 2,797,482 | 7/1957 | Zahn | 433/170 |
| 2,798,294 | 7/1957 | Zahn | 433/170 |
| 3,019,528 | 2/1967 | Pietro | 433/170 |
| 3,023,500 | 3/1962 | Prosen | 433/170 |
| 3,267,574 | 8/1966 | Oddo | 433/170 |
| 3,999,297 | 12/1976 | Globe | 433/170 |
| 4,009,519 | 3/1977 | Hallmark | 433/170 |
| 4,014,094 | 3/1977 | Schumann | 433/170 |

Primary Examiner—Robert Peshock
Attorney, Agent, or Firm—Max E. Shirk

[57] ABSTRACT

A first hinge member has a serrated shank affixed to a dental restoration section and a spherical pivot-head at the free end of the shank; a pair of oppositely-open, axially-aligned, hemispherical bearing cups are provided on the pivot head for engagement by hemispherical trunnions provided on the inner wall of a substantially spherical cap forming part of a second hinge member affixed to a clasp section engaging an abutment tooth; a downwardly-open semi-cylindrical stop member is affixed to the cap in overlying relationship with the free end of the shank for engagement thereby to limit relative movement between the restoration section and the endentulous ridge portion of a user's mouth.

3 Claims, 5 Drawing Figures

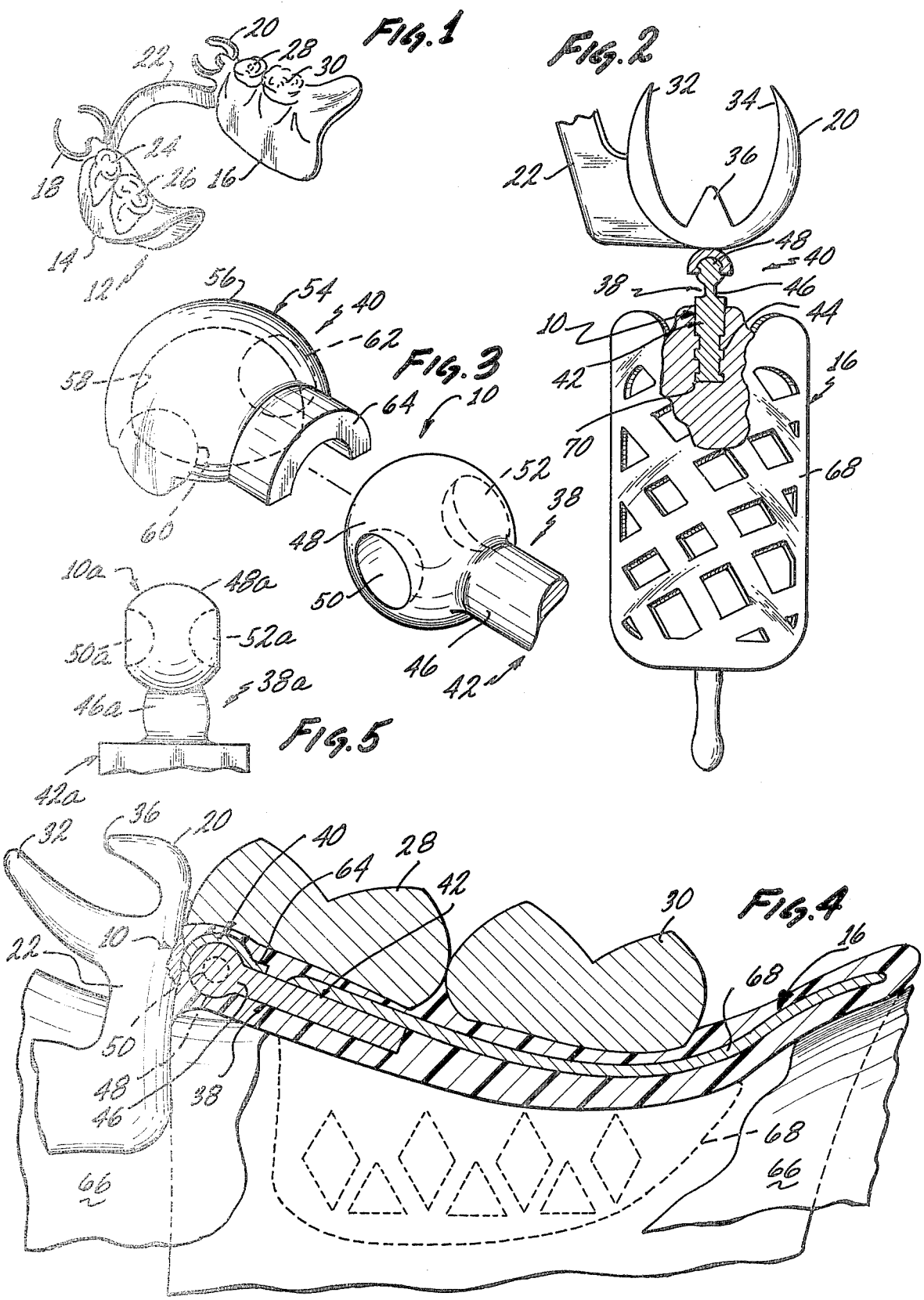

STRESS-RELIEVING HINGE FOR A DENTAL RESTORATION

BACKGROUND OF THE INVENTION

The background of the invention will be set forth in two parts.

1. Field of the Invention

The present invention relates generally to dental restorations and more particularly to an improved stress-relieving hinge connecting a tooth clasp to a restoration section adapted to cover the endentulous ridge in a user's mouth.

2. Description of the Prior Art

The prior art known to applicants is listed by way of illustration, but not of limitation, in separate communications to the United States Patent and Trademark Office. This prior art includes U.S. Pat. No. 2,797,482 which discloses two embodiments of a stress-relieving hinge.

In a first embodiment, a T-shaped hinge part includes a flat, rectangular shank and a cylindrical pivot head. The pivot head is formed integrally with the shank at one end thereof with its major axis lying normal to the major axis of the shank. The other end of the shank has a pair of notches that aid mechanical joinder with a metal saddle which may be cast to the shank. The ends of the pivot head are provided with a pair of axially aligned conical sockets which have been oxidized. A second hinge part is then formed according to the lost wax method and includes a trunnion in pivotal engagement with each conical recess and trunnion heads which are joined to a stop bar spanning the free end of the shank closely adjacent the cylindrical pivot head.

The second embodiment of a stress-relieving hinge disclosed in U.S. Pat. No. 2,797,482 includes a first hinge member having a cylindrical shank, which is provided with a notch, and a spherical head, which is formed on the shank at its end which is opposite the notch. The notched end of the shank is embedded in a metallic boss on a skeleton saddle.

During the waxing-in stage of the production of a dental appliance using this hinge, the spherical head is encased in a wax coating having a stop that overlies the uncovered portion of the spherical head adjacent the shank. This waxed-up assembly is then waxed into a wax model of a tooth clasp so that a second hinge member may be formed on the first hinge member and the tooth clasp during a burning-out operation.

While generally satisfactory, these prior art stress-relieving hinges do have certain disadvantages.

One disadvantage with the hinge having the cylindrical pivot head and a stop bar spanning the shank closely adjacent the pivot head resides in the fact that an excessive amount of the tooth which overlies the hinge must be ground away when this tooth is ground into position. Another disadvantage resides in the fact that food may enter the space between the stop bar and the pivot head.

One disadvantage with the hinge having the spherical head resides in the fact that it is subject to lateral movement permitting the attached saddle to irritate lingual and buccal tissue in the user's mouth.

SUMMARY OF THE INVENTION

In view of the foregoing factors and conditions characteristic of stress-relieving hinges for dental restorations, it is a primary object of the present invention to provide a new and useful stress-relieving hinge not subject to the disadvantages enumerated above and having improved hinge elements which may be used in a dental restoration efficiently, safely and expeditiously.

According to the present invention, an improved stress-relieving hinge is provided between a clasp section and a restoration section in a dental restoration.

The hinge includes a first hinge member having a serrated shank affixed to the restoration section and a spherical pivot head at the free end of the shank. The pivot head is provided with an oppositely-open pair of axially-aligned, hemispherical bearing cups.

The hinge also includes a second hinge member having a substantially spherical cap affixed to the clasp section and encompassing the pivot head with a pair of axially-aligned, hemispherical trunnions provided on the inner wall of the cap in working engagement with the bearing cups. A semi-cylindrical stop member is affixed to the cap in overlying relationship with the exposed portion of the shank for engagement thereby to limit relative movement between the restoration section and the endentulous ridge of a user's mouth.

It is an important feature of the invention that the longitudinal axis of the hinge be parallel to, and remain centered with respect to, the crest of the ridge when the dental restoration is in position in a user's mouth to prevent soreness caused by the restoration section pressing into lingual and buccal tissue.

The features of the present invention which are believed to be novel are set forth with particularity in the appended claims. The present invention, both as to its organization and manner of operation, together with further objects and advantages thereof, may best be understood by reference to the following description, taken in connection with the accompanying drawings in which like reference characters refer to like elements in the several views.

BRIEF DESCRIPTION OF THE DRAWINGS

FIG. 1 is a perspective view of a dental restoration employing stress-relieving hinges of the present invention;

FIG. 2 is a partial plan view, with parts broken away to show internal construction, of the metal saddle, hinge and tooth clasp portions of one-half of the dental restoration shown in FIG. 1;

FIG. 3, is an enlarged, partial, exploded perspective view of the hinge shown in FIG. 2;

FIG. 4 is an enlarged cross-sectional view of one-half of the dental restoration shown in FIG. 1; and FIG. 5 is a plan view of a modified shank for a stress-relieving hinge of the present invention.

DESCRIPTION OF THE PREFERRED EMBODIMENTS

Referring again to the drawings and more particularly to FIGS. 1-4, a stress-relieving hinge constituting a presently-preferred embodiment of the invention, generally designated 10, is shown in combination with a dental restoration 12 (FIG. 1) including first and second restoration sections 14, 16, first and second clasp sections 18, 20 and a lingual bar 22. The restoration sections 14, 16 are each molded from a suitable plastic material to conform to the shape of an endentulous ridge in a user's mouth. Restored posterior teeth, such as those shown at 24, 26, 28 and 30, may be held in position by this plastic material.

The clasp sections 18, 20 each includes a pair of ring clasp arms 32, 34 and an occlusal rest 36 and are connected together into a unitary structure by the lingual bar 22. Each clasp section is connected to its associated restoration section by a hinge 10 to relieve the stress on the abutment teeth (not shown) to which the clasp sections are adapted to be attached.

Each hinge 10 includes a first hinge member 38 and a second hinge member 40. The first hinge member 38 includes a rectangular shank 42 having a plurality of serrations 44 provided at one end and a cylindrical portion 46 at its other end which carries a spherical pivot head 48 provided with an oppositely-open pair of axially-aligned, hemispherical bearing cups 50, 52. The second hinge member 40 includes a substantially spherical cap 54 having an encompassing sidewall 56 on the inner surface 58 of which are provided a pair of axially-aligned, hemispherical trunnions 60, 62 adapted to workingly engage bearing cups 50, 52, respectively. A downwardly-open, semi cylindrical stop member 64 is affixed to cap 54 in overlying relationship with cylindrical portion 46 of shank 42 for engagement thereby to limit relative movement between restoration section 16 and endentulous ridge 66.

As best shown in FIGS. 2 and 4, dental restoration 12 also includes a metal saddle skeleton 68 which, in a manner well known to dental technicians and dentists, is embedded within the plastic portion of the dental restoration. It will be apparent to those skilled in the art that saddle skeleton 68, lingual bar 22 and clasp sections 18, 20 comprise a metallic framework which may be made from any suitable precious metal or a chrome-cobalt-molybdenum alloy. This metallic framework may be produced in accordance with the lost-wax method in the manner described in U.S. Pat. No. 2,797,482. Additionally, the second hinge member 40 may be supplied to a dental technician in the form of a plastic member pivotally connected to pivot head 48 on shank 46, which are also metal members.

During the waxing-in process upon a model and after the clasp sections 18, 20, lingual bar 22 and saddle skeleton 68 have been formed, hinge 10 is placed in the mold with its longitudinal axis lying parallel to, and centered with respect to, the center of the crest of ridge 66. Wax is placed around serrations 44 on shank 42 to form a wax boss pattern on waxed-in saddle 68. Plastic cap 54 is joined to clasp sections 18, 20 by another wax boss pattern.

The wax and plastic may then be driven off during an old and well-known burning-out operation in an oven. At this time, the exposed portions of the first hinge member 38 becomes oxidized so that, during a subsequent metal-casting operation, the metal that becomes cap 54 and trunnions 60, 62 will not fuse to the pivot head 48 and bearing cups 50, 52, respectively, leaving the first and second hinge members free for pivotal movement with respect to each other. Trunnions 60, 62 also shrink slightly to produce a freer hinge. The serrated end of shank 42, which is also oxidized, receives the fluid metal so that when the latter cools it shrinks into a tight joinder and despite the fact that fusion does not actually take place, a sufficiently rigid joint takes place and a practically immovable anchor of shank 42 in boss 70 of saddle skeleton 68 takes place.

A modified first hinge member is shown in FIG. 5 at 38a and includes a rectangular shank 42a, a pivot head 48a, bearing cups 50a, 52a and an elliptical shank portion 46a. Hinge member 38a differs from hinge member 38 in that the cylindrical shank portion 46 of hinge member 38 is replaced by the elliptical shank portion 46a of hinge member 38a for increased strength.

While the particular stress-relieving dental restoration hinge herein shown and described in detail is fully capable of attaining the objects and providing the advantages hereinbefore stated, it is to be understood that it is merely illustrative of the presently-preferred embodiment of the invention and that no limitations are intended to the details of construction or design herein shown other than as defined in the appended claims which form a part of this disclosure.

Whenever the term "means" is employed in these claims, this term is to be interpreted as defining the corresponding structure illustrated and described in this specification or the equivalent of the same.

What is claimed is:

1. In a dental restoration having a clasp section to engage an abutment tooth, a restoration section to cover an endentalous ridge of the mouth, and a stress-relieving hinge therebetween, the improvement which comprises:

a first hinge means having a shank affixed to said restoration section and a spherical pivot head at the free end of said shank, said spherical pivot head being provided with an oppositely-open pair of axially-aligned bearing cups;

a second hinge means including a substantially spherical cap affixed to said clasp section encompassing said pivot head and having a pair of axially-aligned, trunnions provided on the inner wall of said cap and positioned in said bearing cups, said bearing cups and said trunnions being hemispherical shaped to limit lateral movement of said restoration section during articulation of said hinge; and a stop means affixed to said cap in overlying relationship with said free end of said shank for engagement thereby to limit relative movement between said restoration section and said ridge, said shank having a flat rectangular shape, said pivot head being joined to said shank by a cylindrically-shaped shaft portion, said stop means comprising a downwardly-open, semi-cylindrical member overlying said cylindrically-shaped shaft portion.

2. An improvement as stated in claim 1 wherein said stress-relieving hinge is connected to said clasp section and to said restoration section in a manner such that the longitudinal axis of said hinge lies parallel to, and is centered with respect to, the crest of said endentulous ridge.

3. A stress-relieving hinge adapted to be installed by a dental technician between a clasp section and a restoration section of a dental restoration, comprising:

a metal hinge section having a flat, serrated rectangular shank adapted to be affixed to a metal-skeleton-saddle portion of said restoration section by a metal boss shrunk-fit to said serrations and a spherical pivot head joined to the free end of said rectangular shank by a cylindrical shaft portion, said spherical pivot head being provided with an oppositely-open pair of axially-aligned, hemispherically-shaped bearing cups;

a plastic hinge section articulately mounted on said pivot head, said plastic hinge section including a substantially spherical cap having an inner wall encompassing said pivot head and a pair of axially-aligned, hemispherically-shaped trunnions extending from said inner wall into working engagement with said bearing cups on said pivot head; and
a downwardly-open, semi-cylindrical, plastic stop member formed integrally with said cap in overlying relationship with said cylindrical shaft portion to limit articulating movement of said cap in one direction.

* * * * *